United States Patent [19]

Schulte

[11] 4,369,190

[45] Jan. 18, 1983

[54] ANALGESIC COMPOSITION AND USE THEREOF TO AMELIORATE INTRACTABLE PAIN

[76] Inventor: Thomas L. Schulte, 218 Family Farm Dr., Woodside, Calif. 94062

[21] Appl. No.: 276,566

[22] Filed: Jun. 23, 1981

[51] Int. Cl.³ ............... A61U 31/10; A61U 31/235
[52] U.S. Cl. ............................ 424/308; 424/337
[58] Field of Search ........................ 424/308, 337

[56] References Cited

U.S. PATENT DOCUMENTS 3,551,554  8/1968  Hershler .................. 424/337
4,073,897  2/1978  Karlor ..................... 424/230

*Primary Examiner*—Stanley J. Friedman
*Attorney, Agent, or Firm*—Millen & White

[57] ABSTRACT

Intractable pain is ameliorated by the topical application proximate the situs of the pain of an analgesic amount of a liquid mixture of DMSO and of biphenamine in a pharmaceutically acceptable carrier, the concentration of DMSO and biphenamine in the mixture each being ineffective to ameliorate the pain when applied separately from the other to the situs. The mixture is also useful for the amelioration of pathological conditions of the skin and other topical areas of the body caused by viral, bacterial, fungal and other microorganism infections and localized inflammatory conditions generally which cause itching or pain.

13 Claims, No Drawings

ANALGESIC COMPOSITION AND USE THEREOF TO AMELIORATE INTRACTABLE PAIN

BACKGROUND OF THE INVENTION

This invention relates to novel topical analgesic compositions and to their use to alleviate intractable pain.

The treatment of localized intractable pain topically with analgesics historically has not met with significant success, primarily because the surface presented by the affected area, typically skin or mucous membrane, provides an effective barrier to the analgesic agent reaching the situs of the pain. Therefore, physicians must resort to injections to achieve adsorption of the analgesic, which usually also requires that the analgesic agent be in a vehicle which retards the rate of absorption, or to the oral administration of systemic analgesic agents, such as the barbituates. Both of these approaches have obvious limitations and pose well-known problems. There therefore is a long standing need for an effective topical analgesic agent which is effective in ameliorating localized intractable pain and can safely be applied to the situs of the pain by the person in pain.

The compositions of this invention comprise biphenamine ($\beta$-diethylaminoethyl 3-phenyl-2-hydroxybenzoate) base or pharmaceutically acceptable acid addition salt thereof. Salts of this compound are known to have a variety of activities, including local anesthetic (U.S. Pat. No. 1,976,922); treatment of seborrhea (U.S. Pat. No. 3,123,531); as well as antihistaminic and bactericidal activity and fungicidal properties (U.S. Pat. No. 2,594,350; Report Annual Meeting So. Med. Assoc., Nov. 6, 1961).

Biphenamine hydrochloride has been sold as a 1% ointment, under the trademark "Melsaphine," as a topical anesthetic agent possessing bactericidal, fungicidal and antihistamine properties and as a 1% aqueous shampoo under the trademark "Alvininex," Federal Register, Vol. 34, No. 189, page 153, Oct. 2, 1969.

Although its use for treating arthritis and related conditions is claimed in U.S. Pat. No. 4,073,897, nothing was known concerning its topical analgesic activity or its usefulness for the treatment of localized intractable pain because the compound is ineffective for ameliorating intractable pain by the topical application thereof, in the absence of a tissue penetrant such as DMSO.

The compositions of this invention also comprise DMSO (dimethyl sulfoxide). U.S. Pat. No. 3,551,554 and 3,711,602 disclose that DMSO is effective as an agent for enhancing tissue penetration of physiologically active agents. U.S. Pat. No. 3,549,770 discloses (Example 36) the topical application of a mixture of acetylsalicylic acid and DMSO is more effective than DMSO alone to relieve the pain and muscle spasm of rheumatoid spondylitis. See also U.S. Pat. No. 3,711,602, 3,711,606 and 3,743,727 and references cited therein. These patents disclose that the tissue penetration of physiologically active compounds, inter alia, steroidal agents and certain antimicrobial agents, can be enhanced with DMSO. U.S. Pat. No. 3,740,420 discloses DMSO compositions for topical administration containing thickening agents.

The foregoing patents disclose that concentrations of DMSO of 10% by weight and above can effect penetration of such agents through various mucous membrane barriers and that concentrations of 50% by weight and above are effective to achieve penetration thereof through the skin. DMSO is also known to enhance the antiperspirant activity astringent of aluminum, zinc and zirconium salts (U.S. Pat. No. 3,499,961).

DMSO has been disclosed as useful for treating a variety of pathological conditions. U.S. Pat. No. 3,549,770 discloses topical application as a particularly advantageous route. This patent claims methods of relieving the signs and symptoms of tissue inflammation; of vascular insufficiency in the blood and lymph circulatory system; of respiratory distress; of arthritis and a method of promoting tissue repair, by administering an effective amount of DMSO, preferably topically. Dosages as low as 0.01 g/kg and up to 1.0 g/kg per day and sometimes higher dosages are contemplated with 0.1–0.2 g/kg individual doses being average. Higher concentrations of DMSO, such as at least 25% and more often at least about 50% are preferred for topical application. Treatment of pain, including "phantom pain," with DMSO preferably by direct application to the involved area is expressly contemplated. In one example (Example 27) the pain associated with skin abrasion was relieved with 15% DMSO in isotonic saline. 10% to 90% water solutions of DMSO, preferably 20% to 40%, in water, alcohol or glycerine are useful for topical application to the mucous membranes of the body although ". . . lower concentrations of DMSO say down to 3% by weight may be useful in some instances."

The use of DMSO as an ataratic agent is disclosed in U.S. Pat. No. 3,790,682. Pharmaceutical compositions containing DMSO and thickening agents are disclosed in U.S. Pat. No. 3,740,420, along with their use to treat and repair damaged tissue, as an antiinflammatory agent, as an analgesic agent, as a muscle relaxant, as an agent for treating vascular insufficiency, and relieve the signs and symptoms of certain specific syndromes, viz., respiratory distress, arthritis and burns. None of the foregoing references disclose or suggest that intractable pain can be treated with low concentrations of DMSO, e.g., topically on the skin at cncentrations below 10%, although U.S. Pat. No. 3,549,770 discloses (Col. 10, lines 42–49) that for pharyngitis or hiccups, the subject may gargle with a more dilute aqueous solution, e.g., containing 1% or preferably 10% by weight of DMSO, and (Col. 28, lines 44–56) that concentrations of DMSO down to 3% by weight may be useful in some instances, with 10% to 90% water solutions being particularly suitable. The effectiveness of DMSO topically for treating pain at concentrations below 10% by weight is not suggested in the prior art. Moreover, I have found that low concentrations of DMSO alone have little if any effect topically upon intractable pain.

SUMMARY OF THE INVENTION

In a method of use aspect, this invention relates to a method for amelioration of intractable pain which comprises applying topically proximate the situs of the pain an analgesically effective amount of a mixture of DMSO and of biphenamine in a pharmaceutically acceptable carrier, the concentration of DMSO and biphenamine in the mixture each being ineffective to ameliorate the pain when applied separately from the other to the situs.

In a composition aspect, this invention relates to an analgesic composition adapted for topical administration and comprising a mixture of DMSO and of biphenamine in a pharmaceutically acceptable carrier, the concentrations of DMSO and of biphenamine or salt thereof in the composition being collectively effective to render the composition capable of ameliorating intractable pain when the composition is applied topically proximate the situs of intractable pain but ineffective for either component of the ingredient to do so in the absence of the other.

DETAILED DISCUSSION

Biphenamine (base or acid addition salt thereof) and DMSO are applied topically to the patient proximate the situs of the intractable pain, viz., to the skin and/or the mucous membrane of the mouth, throat, nasal passages, ear canals and drums, anal or vaginal regions, as a mixture in a pharmaceutically acceptable carrier or diluent, preferably aqueous. The mixture preferably is liquid, e.g., in the form of clear solutions, such as drops, aerosols or sprays, or in the form of lotions or other viscous liquids. The mixture can also be semi-solid or solid, e.g., in the form of ointments, creams, suppositories. Viscosity regulating agents, such as thickeners and gelling agents, e.g., glycerin, sodium carboxymethylcellulose, etc., can also be used to regulate flowability. See. U.S. Pat. Nos. 3,740,420 and 3,711,602, whose disclosures are incorporated herein by reference. They can be in the form of an oil-in-water or water-in-oil emulsion, as disclosed in U.S. Pat. No. 3,740,420, or as a single phase aqueous solution, the latter being preferred. Organic solvents, e.g., ethanol or isopropanol, can also be present.

The DMSO is present in the mixture at a concentration which is not analgesic topically in the absence of the biphenamine, viz., less than 10%, e.g., 3–7%, preferably about 5%. At these concentrations, DMSO exhibits neither the analgesic effect achieved when it is applied to the skin in the absence of the biphenamine nor the side effects observed at higher concentrations, e.g., skin rash.

The biphenamine is present in the liquid mixture at a concentration of up to 1%, e.g., from about 0.1% to 1%, preferably present in the form of a pharmaceutically acceptable salt thereof, e.g., hydrochloride, hydrobromide, sulfate, phosphate, acetate, succinate, tartrate, benzoate, citrate, lactate or maleate, preferably the hydrochloride. Although acid addition salts of biphenamine are disclosed in U.S. Pat. No. 1,976,922 as having local anesthetic activity at a 2% concentration, neither its ability to ameliorate localized intractable pain when applied topically nor its effectiveness at lower concentrations is suggested.

The mixture of DMSO and biphenamine can be applied topically as frequently as every hour or as infrequently as daily or longer, depending on the degree of amelioration of the pain achieved with each application and the duration thereof. The amount applied will depend on such factors as the level and nature of the pain, the degree of localization thereof, the concentration of DMSO and biphenamine therein and the individual's responsiveness to analgesics generally. As little as two or three drops may be effective and as much as a fluid ounce may be required. The effectiveness of successively greater or smaller dosages can determine the optimum effective individual dose.

The compositions of this invention are effective for the amelioration of intractable pain, i.e., pain which is substantially non-responsive to non-sedating systemic analgesics such as aspirin, phenacetin and acetaminophen. The method of this invention is useful for the treatment of localized intractable pain resulting from a wide variety of pathological conditions, e.g., severe sprains, debriding wounds, degenerative disc syndrome, bursitis and burns. The compositions of this invention are also useful for the amelioration of pathological conditions of the skin and other topical areas of the body caused by viral, bacterial, fungal and other microorganism infections and localized inflammatory conditions generally which cause itching or pain, e.g., herpes virus lesions, pain, itching and fungus infections of the perineum, feet, hands, ear canal, inflammation or sclerosis of the ear drum, urinary bladder, abscess cavities, leg ulcers, bed sores, infected sinuses, senile keratosis, animal and insect bites, painful muscle spasms and pain from "pinched nerves."

Contemplated equivalents of the compositions and methods of treating pain of this invention are compositions otherwise corresponding thereto containing a different skin penetrant, e.g., propylene glycol, in place of the DMSO and the use thereof topically to treat intractable pain.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

An aqueous solution of DMSO and biphenamine hydrochloride can be produced by dissolving 50 grams of the former and 1 gram of the latter in 950 cc of sterile isotonic water. The viscosity thereof can be increased with any conventional viscosity enhancing agent, e.g., carboxymethylcellulose.

EXAMPLE 2

A lotion can be formulated in the conventional manner from the following ingredients, after dissolving the biphenamine hydrochloride and buffer in the water.
biphenamine . HCl: 1 gm
DMSO: 50 cc
Cetyl alcohol: 200 gm
Propylene glycol: 100 gm
Sodium laural sulfate: 15 gm
Water q.s. 1000 cc

EXAMPLE 3

An ointment can be produced from the following ingredients, after dissolution of the biphenamine hydrochloride in water.
Biphenamine . HCl: 1 gm
DMSO: 50 cc
Glyceryl monostearate, Acid Type: 180 gm
Stearyl alcohol: 50 gm
Polysorbate 80: 20 gm.
Water q.s. 1,000 cc

EXAMPLE 4

An aqueous alcoholic ointment can be prepared by blending the following ingredients, with the biphenamine hydrochloride first dissolved in the water.
Biphenamine . HCl: 100 mg
DMSO: 5 gm
Ethanol: 10 gm
Corbowax 1,500: 20 gm
Water q.s. 1,000

EXAMPLE 5

Suppositories can be cast from a melt of the following ingredients, after first dissolving the biphenamine hydrochloride in the water.

Biphanamine . HCl: 70 mg
DMSO: 3.4 gm
Sodium stearate: 10 gm
Glycerin: 45 gm
Water: 10 gm

EXAMPLE 6

The acute pain resulting from collapsed discs in the neck of a female age 71 was successfully ameliorated for periods of 1 to 10 hours by the topical application of 1 to 16 drops of the composition of Example 1 to the occiput, the situs of the pain. As a result, the necessity of traction and the wearing of a neck collar which immobilized the neck was eliminated.

EXAMPLE 7

A male age 68 who experienced consistent severe lower back pain after a lumbar disc operation had attempted to no avail to alleviate the pain variously with Percodan, aspirin, 90% DMSO applied topically to the lower back region, and alcohol consumption. Within eight minutes after the application of 8 drops of the composition of Example 1 topically with manual spreading around the lower back at the situs of the pain, the pain was gone and remained eliminated for 8 days. The patient used the composition in this manner off and on at various intervals and found the relief from pain superior to 90% aqueous DMSO, with none of the redness or skin irritation associated with the use of the latter.

The same superior results were achieved with this patient in relieving the pain associated with a sprained knee which was swollen and the knee could not be bent. Several drops of the composition of Example 1 spread around the knee area produced marked relief from the pain occurring within a few minutes. Movement of the knee was possible within a few hours thereafter.

EXAMPLE 8

A 78 year old arthritic patient with a painful knee of unknown etiology obtained immediate relief from the pain after a few drops of the composition of Example 1 was spread on the knee area. Previously, 90% aqueus DMSO had been tried by the patient without much relief.

EXAMPLE 9

The index finger of a 38 year old woman had been damaged by an automatic riveting gun, resulting in severe pain and infection of tendon. Although treatment with 90% DMSO had given some relief, after 9 months she had limited motion in the finger and the pain precluded her use of the riveting gun. Within 24 hours after applying a few drops of the composition of Example 1 to the injured finger, it could be extended nearly to normal position without pain. After repeated treatments over a period of about 2-3 weeks, she had normal movement of the finger without pain.

EXAMPLE 10

A 74 year old artist had such severe bursitis in his right shoulder that he could not paint. He obtained relief from the pain after one application of several drops of the composition of Example 1 to the shoulder area and was able to drive several hundred miles in his automobile. Upon his return, the bursitis flared up again but the pain was ameliorated by a second application.

EXAMPLE 11

A male (66 years) had a virus respiratory and intestinal infection that did not respond to treatment, including vertigo medicine, either for infection or for dizziness. After 6 weeks he was still suffering and toxic and had a sore inflammed throat. He placed a few drops of the composition of Example 1 in his ears and after 2 hours he put ½ teaspoon (2 cc) thereof in a quarter glass of water and gargled with the mixture. Overnight he was greatly improved. He repeated the treatment after 24 hours and 48 hours. He required no further treatment and remained free of symptoms.

EXAMPLE 12

A female (43 years) developed symptoms and clinical condition similar to those of Example 11. Her doctor examined her ears, nose and throat as part of a general physical examination. He also prescribed medication for the dizziness and respiratory and intestinal symptoms, but the condition remained. Drops of the composition of Example 1 were inserted into each ear canal, once a day for 5 days. After the first day, the patient was relieved of the symptoms and after stopping the treatment, the symptoms did not reoccur.

EXAMPLE 13

A male (78 years) had buzzing or ringing in the ears (tinnitus) for 50 years. All treatments and medicines failed and the symptoms became increasingly bothersome with age. All treatment failed. He also had a fungus infection in both ear canals. Drops of the composition of Example 1 were applied 4 times in one day, from late afternoon until bedtime. The next morning there was a change in the tone of the tinnitus which appeared to be ameliorated by the treatment.

EXAMPLE 14

A male (39 years) twisted his spine and displaced a thoracic disc in his back while riding a horse. He developed a severe spasm and swelling of the erector spinae muscles on the left side of his back. He had to lie flat on his back to relieve the pain and could not walk without stooping over. The composition of Example 1 was applied to the area of tenderness in his back. Within 15 minutes there was a definite improvement in the severity of the pain. Another application was made ½ hour later and a third 1 hour after that. He developed a slight redness at the site of application, which appeared to be the result of an increase in the capillary circulation rather than an irritation of the skin. There was no pain, no itching, no burning and no discomfort and he was entirely comfortable.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the amelioration of intractable pain which comprises applying topically proximate the situs of the pain an analgesically effective amount of a mixture of less than 10% by weight of DMSO and of biphenamine in a pharmaceutically acceptable carrier, the concentration of DMSO and biphenamine in the mixture each being ineffective to ameliorate the pain when applied separately from the other to the situs.

2. A method according to claim 1 wherein the mixture is applied to the skin.

3. A method according to claim 1 wherein the DMSO is present in the mixture at a concentration of about 5%.

4. A method according to claim 1 wherein the biphenamine is present in the mixture as a pharmaceutically acceptable acid addition salt thereof at a concentration of about 0.1% to 1% and the DMSO is present therein at a concentration of 3–78%.

5. A method according to claim 1 wherein the biphenamine is present in the mixture as a pharmaceutically acceptable acid addition salt thereof at a concentration of about 0.5%.

6. A method according to claim 2 wherein the mixture is an aqueous solution of DMSO at a concentration of about 5% and of biphenamine hydrochloride at a concentration of about 0.5%.

7. A method according to claim 1 wherein the pain is metastatic carcenoma bone pain.

8. A method according to claim 1 wherein the pain is joint pain caused by rheumatoid arthritis.

9. An analgesic composition adapted for topical administration and comprising a mixture of DMSO and of biphenamine in a pharmaceutically acceptable carrier, the concentrations of DMSO and of biphenamine in the composition being less than 10% and up to 1%, respectively, said concentrations being collectively effective to render the composition capable of ameliorating intractable pain when the composition is applied topically proximate the situs of intractable pain but ineffective for either component of the ingredient to do so in the absence of the other.

10. A composition of claim 9 wherein the concentration of the DMSO therein is about 5%.

11. A composition of claim 10 wherein the biphenamine is present as a pharmaceutically acceptable salt thereof at a concentration therein of about 0.1% to 1% and the DMSO is present at a concentration therein of 3–7%.

12. A composition of claim 10 wherein the biphenamine is present as a pharmaceutically acceptable salt thereof at a concentration of about 0.5%.

13. A composition of claim 12 wherein the mixture is an aqueous solution of DMSO at a concentration of about 5% and of biphenamine hydrochloride at a concentration of about 0.5%.

* * * * *